United States Patent [19]
Trickes

[11] Patent Number: 5,763,603
[45] Date of Patent: Jun. 9, 1998

[54] CRYSTALLINE TAZOBACTAM, AND ITS PRODUCTION AND USE

[75] Inventor: Georg Trickes, Loerrach, Germany

[73] Assignee: Taiho Pharmaceutical Co., Ltd., Tokyo, Japan

[21] Appl. No.: 403,829

[22] PCT Filed: Nov. 2, 1994

[86] PCT No.: PCT/JP94/01855

§ 371 Date: Mar. 21, 1995

§ 102(e) Date: Mar. 21, 1995

[87] PCT Pub. No.: WO95/12601

PCT Pub. Date: May 11, 1995

[30] Foreign Application Priority Data

Nov. 6, 1993 [EP] European Pat. Off. .............. 93118016

[51] Int. Cl.$^6$ .................. C07D 499/00; A61K 31/425
[52] U.S. Cl. ............................. 540/310; 514/210
[58] Field of Search ..................... 540/310; 514/210

[56] References Cited

U.S. PATENT DOCUMENTS

| | | | |
|---|---|---|---|
| 4,562,073 | 12/1985 | Micetich et al. | 424/114 |
| 4,774,238 | 9/1988 | Brown et al. | 514/192 |
| 4,912,211 | 3/1990 | Bonfanti | 540/222 |

FOREIGN PATENT DOCUMENTS 63-66187  3/1988  Japan.

OTHER PUBLICATIONS

Chemical Patents Index Basic Abstracts Journal, Section B:FARMDOC, 1988, Derwent Publications, week 8818, 29 Jun. 1988, 88–122648/18.

Primary Examiner—Mukund J. Sham
Assistant Examiner—Pavanaram K. Sripada
Attorney, Agent, or Firm—Sughrue, Mion, Zinn, Macpeak & Seas, PLLC

[57] ABSTRACT

Crystalline sodium 2α-methyl-2β-(1,2,3-triazol-1-yl)-methylpenam-3α-carboxylate-1,1-dioxide monohydrate (crystalline tazobactam sodium monohydrate) obtainable by adding to a concentrated aqueous solution of sodium 2α-methyl-2β-(1,2,3-triazol-1-yl)-methylpenam-3α-carboxylate-1,1-dioxide (tazobactam sodium) a solvent selected from acetone and ethanol in an amount corresponding to a solvent to water ratio of between about 95:5 and 99:1 v/v and crystallizing the desired product from the solvent mixture. The crystalline tazobactam sodium monohydrate exhibits a high β-lactamase inhibitory activity in combination with β-lactam antibiotics.

30 Claims, 4 Drawing Sheets

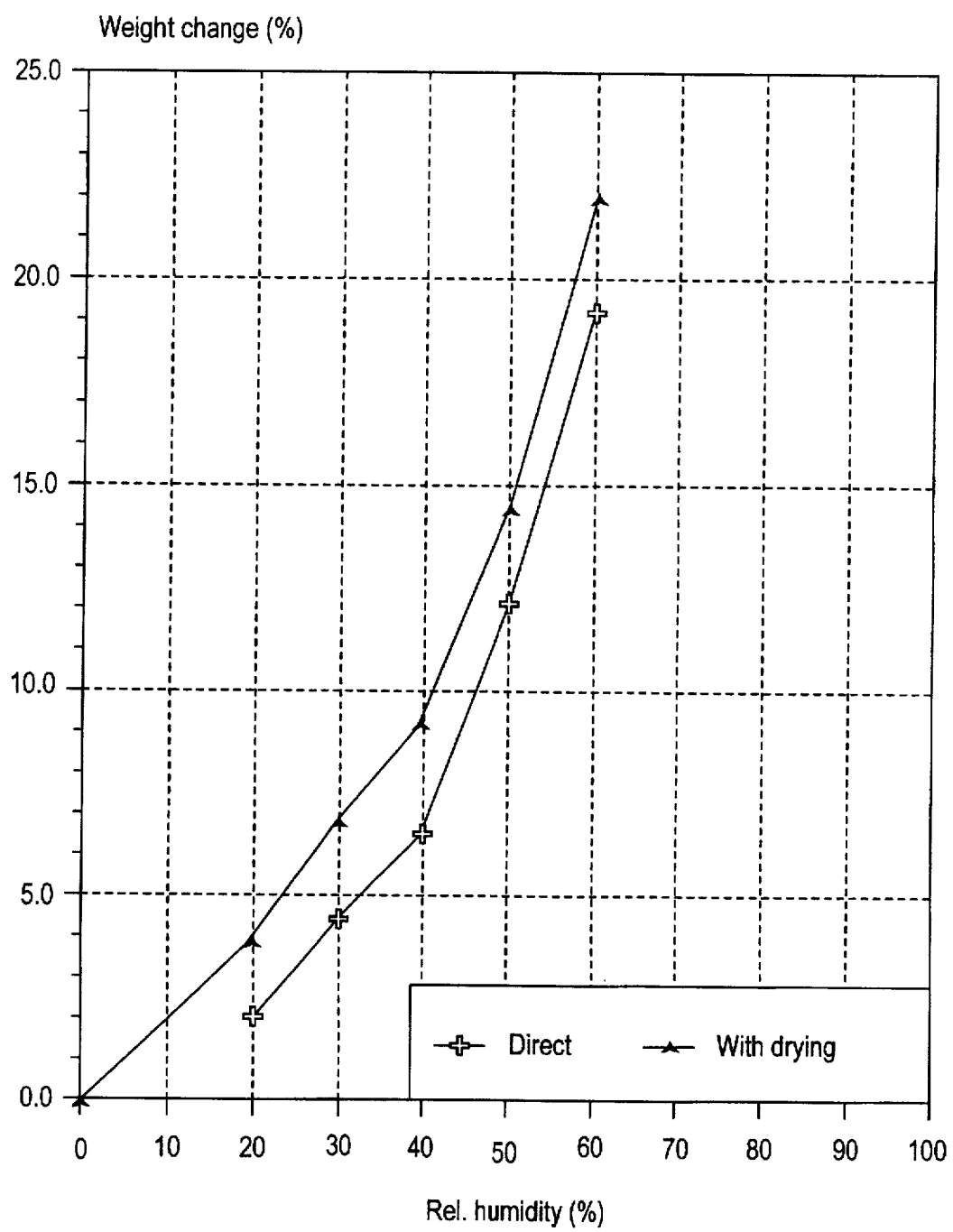

FIG. 3-2

| No. | 2THETA | d | REL I (%) | MAX I | INTEQ I | WIDTH |
|---|---|---|---|---|---|---|
| 1 | 10.201 | 8.6645 | 25.2 | 665. | 3864.75 | 0.136 |
| 2 | 11.300 | 7.8242 | 86.8 | 2290. | 16519.83 | 0.169 |
| 3 | 13.820 | 6.4026 | 78.2 | 2063. | 13733.20 | 0.156 |
| 4 | 16.300 | 5.4336 | 57.4 | 1514. | 10184.79 | 0.158 |
| 5 | 16.759 | 5.2858 | 28.1 | 743. | 4429.26 | 0.140 |
| 6 | 18.141 | 4.8862 | 41.5 | 1096. | 7140.80 | 0.153 |
| 7 | 18.459 | 4.8027 | 89.2 | 2355. | 15620.33 | 0.156 |
| 8 | 18.979 | 4.6723 | 46.5 | 1227. | 8882.84 | 0.170 |
| 9 | 20.061 | 4.4226 | 100.0 | 2639. | 17900.20 | 0.159 |
| 10 | 21.439 | 4.1414 | 55.0 | 1451. | 10217.94 | 0.165 |
| 11 | 22.679 | 3.9177 | 37.1 | 979. | 8503.04 | 0.204 |
| 12 | 23.060 | 3.8538 | 18.8 | 497. | 2898.12 | 0.137 |
| 13 | 23.341 | 3.8080 | 16.1 | 425. | 2749.36 | 0.152 |
| 14 | 23.600 | 3.7668 | 13.7 | 362. | 2051.66 | 0.133 |
| 15 | 24.739 | 3.5959 | 67.3 | 1776. | 12319.30 | 0.163 |
| 16 | 25.779 | 3.4532 | 72.7 | 1918. | 11995.60 | 0.147 |
| 17 | 26.180 | 3.4012 | 28.7 | 758. | 4715.22 | 0.146 |
| 18 | 26.421 | 3.3707 | 25.7 | 679. | 4261.59 | 0.147 |
| 19 | 27.919 | 3.1931 | 57.4 | 1514. | 11184.21 | 0.173 |
| 20 | 28.340 | 3.1467 | 12.6 | 333. | 3437.75 | 0.243 |
| 21 | 29.079 | 3.0683 | 39.8 | 1050. | 7290.46 | 0.163 |
| 22 | 30.380 | 2.9398 | 22.4 | 592. | 4301.54 | 0.171 |
| 23 | 30.640 | 2.9155 | 13.1 | 346. | 2048.06 | 0.139 |
| 24 | 31.178 | 2.8664 | 28.6 | 755. | 4686.16 | 0.146 |
| 25 | 31.399 | 2.8467 | 17.2 | 455. | 2606.58 | 0.135 |
| 26 | 32.137 | 2.7830 | 8.2 | 218. | 1603.78 | 0.173 |
| 27 | 32.779 | 2.7300 | 20.5 | 541. | 3751.11 | 0.163 |
| 28 | 33.261 | 2.6915 | 19.1 | 503. | 3562.67 | 0.166 |
| 29 | 34.299 | 2.6124 | 14.6 | 385. | 2552.69 | 0.156 |
| 30 | 34.480 | 2.5991 | 16.1 | 424. | 2592.66 | 0.144 |
| 31 | 35.680 | 2.5144 | 30.2 | 797. | 5869.09 | 0.173 |
| 32 | 36.240 | 2.4768 | 20.4 | 537. | 3974.05 | 0.174 |
| 33 | 36.819 | 2.4392 | 30.6 | 808. | 5662.38 | 0.165 |
| 34 | 37.140 | 2.4188 | 11.7 | 309. | 1724.79 | 0.131 |
| 35 | 38.320 | 2.3470 | 7.4 | 196. | 1844.75 | 0.221 |
| 36 | 39.400 | 2.2851 | 14.4 | 380. | 3142.37 | 0.194 |

I = INTENSITY

CRYSTALLINE TAZOBACTAM, AND ITS PRODUCTION AND USE

TECHNICAL FIELD

The present invention relates to a novel crystalline penicillin derivative, crystalline 2α-methyl-2β-(1,2,3-triazol-1-yl)-methylpenam-3α-carboxylic acid-1,1-dioxide, and its production and use in a medicine.

BACKGROUND ART

In EPOS 97 446 certain penicillin derivatives are disclosed; in particular, 2α-methyl-2β-(l1,2,3-triazol-1-yl)-methylpenam-3α-carboxylic acid-1,1-dioxide of the formula

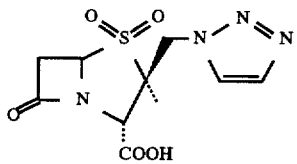

COOH (hereinbelow "tazobactam") and its pharmaceutically acceptable salts, notably the sodium salt, are reported to be useful as β-lactamase inhibitory agents in combination with known β-lactam antibiotics, viz. increasing the antimicrobial activity of the β-lactam antibiotics.

However, up to the present tazobactam sodium has been obtained in solid form only in the amorphous state, e.g. as a lyophilisate. Such solid forms are hygroscopic, possess inferior stability, and their purification require laborious, e.g. lyophilizing procedures.

Thus, there is a need for a crystalline modification of tazobactam sodium, which overcomes all these drawbacks.

Initial attempts to crystallize the product did not offer the required result: Due to the high solubility of tazobactam sodium in water it was not expected that the product could be crystallized from an aqueous medium. This assumption was supported by findings, according to which concentrated aqueous tazobactam sodium solutions could not be crystallized from methanol due to the solubility of the product in that solvent; moreover, attempts with methyl ethyl ketone/water 95:5 v/v and with ethyl acetate/water 95:5 v/v as solvent failed due to a separation of phases, without crystallization. Therefore, crystallization in the absence of water was attempted: Based on a known procedure, tazobactam was suspended in methanol, and one equivalent of sodium 2-ethylhexanoate solution in ethyl acetate added. To the resulting solution, a less polar solvent was added in order to cause crystallization. The following solvents were investigated: toluene, t-butylmethyl ether, diethyl ether, dimethoxy ethane, i-propanol and ethyl acetate. In all cases, amorphous materials were isolated, which were very hygroscopic and contained water and solvent residues.

DISCLOSURE OF THE INVENTION

However, contrary to expectation, it has surprisingly turned out that a crystalline modification of tazobactam sodium, viz. crystalline sodium 2α-methyl-2β-(1,2,3-triazol-1-yl)-methylpenam-3α-carboxylate-1,1-dioxide monohydrate (crystalline tazobactam sodium monohydrate) can be prepared from an aqueous medium by a particular process which involves a careful balance between the water and one of the organic solvents acetone and ethanol. Thus the process of the present invention for producing crystalline sodium 2α-methyl-2β-(1,2,3-triazol-1-yl)-methylpenam-3α-carboxylate-1,1-dioxide monohydrate (crystalline tazobactam sodium monohydrate) is characterized by adding to a concentrated aqueous solution of sodium 2α-methyl-2β-(1,2,3-triazol-1-yl)-methylpenam-3α-carboxylate-1,1-dioxide (tazobactam sodium) a solvent selected from acetone and ethanol in an amount corresponding to a solvent to water ratio of between about 95:5 v/v and about 99:1 v/v and crystallizing the desired product from the solvent mixture.

The tazobactam sodium can be obtained in accordance with a method described, for example, in EPOS 97 446.

The concentrated aqueous solution of tazobactam sodium used for this crystallization process should contain about 0.1 to 0.4 g, preferably about 0.25 to 0.35 g of water per g of tazobactam equivalent present.

The ratio of acetone or ethanol to water is critical. Already at a ratio of 9:1 v/v it is not possible to crystallize the product even at −20° C. Suitable ratios for crystallization are about 95:5 to 99:1 v/v. Preferred ratios are about 96:4 to 98:2, particularly about 97:3. The crystallization is preferably carried out at a temperature of about −10 ° to +30° C., more preferably +5° C. to a room temperature, for about 1 to 30 hours.

The most preferable solvent is acetone. The acetone, in the amount dictated by the above recommended acetone to water ratio, can be added at once and the mixture be left for a sufficient time, e.g. about 10 to 30 hours to crystallize.

However, preferably the acetone to be added is divided in 3 volumes, which are added successively to the concentrated aqueous tazobactam solution a about room temperature. The first volume is about 23 to 27% of the total acetone volume, the second volume is about 24 to 28% of the total acetone volume and the third volume is about 46 to 52% of the total acetone volume preferably, the first volume is about 24 to 25% of the total acetone volume, the second volume is about 26to 27% of the total acetone volume and the third volume is about 48 to 50% of the total acetone volume. The first volume is preferably added together with a small volume of methanol so as to postpone crystallization until the addition of the second volume. To that end the methanol added to the first volume of acetone is preferably about 1 to 4% v/v of the acetone totally added. The second volume of acetone will start crystallization which can be promoted by scratching the wall of the vessel or by seeding with a small amount of tazobactam sodium monohydrate seed crystals. After addition of the third volume of acetone the crystal yield can be improved by cooling the mixture, e.g. to a temperature in the range of about −10° to +10° C.

Generally, the crystals of tazobactam sodium monohydrate are left after formation to equilibrate with the solvent for a sufficient time, e.g. about 1 to 30 hours, and afterwards isolated in conventional manner, e.g. by filtration, washed with acetone and dried at slightly elevated temperature, e.g. at about +25° to +40° C., preferably under reduced pressure.

Undesirable decomposition of the product is avoided by carrying out the crystallization at about room temperature or below and drying at the above mentioned temperature and pressure.

Crystalline tazobactam sodium monohydrate is a novel compound which is, in contradistinction to the known lyophilisate mentioned above, not hygroscopic and considerably more stable upon storage.

The non-hygroscopic properties of crystalline tazobactam sodium monohydrate are evaluated in accordance with the following measurement method and its results are shown by FIGS. 1 and 2 reporting water absorption by thermogravimetry. FIG. 1 shows that the lyophilisate took up water continuously up to 20% of its own weight with a relative humidity increasing to 60%. In contrast, FIG. 2 shows that crystalline tazobactam sodium monohydrate did not bind water until a relative humidity of 60%. At higher relative humidity the salt was dissolved by the water.

Method of measurement

This measurement was carried out in accordance with a method described, for example, in IYAKUHIN KENKYU, vol. 21, no. 1, pp. 110–125 (1990).

1. With drying

The substance (tazobactam Na-salt lyophilisate according to EPOS 97 446or crystalline tazobactam Na-salt monohydrate according to the present invention) was dried over concentrated sulfuric acid to constant weight and subsequently conditioned to constant weight in air with defined relative humidity. The weight change was calculated 2. Direct The substance was conditioned to constant weight in air with defined relative humidity The weight change was calculated.

The higher stability of the crystalline salt as compared with the lyophilisate was illustrated as follows:

250 mg ampoules containing the crystalline salt and the lyophilisate, respectively, were compared after 14 days of storage at various temperatures. Basis for the composition is the percentage of the decomposition product (2S 3S)2-amino-3-methyl-3-sulfino-4-(1H-1,2,3-triazol-1-yl)-butyric acid (measured by HPLC i.e. High Pressure Liquid Chromatography) the following table reports these percentages after 14 days at the conditions indicated:

hydrate can be used for treating infections disease of human beings and other mammals.

The compound of the invention, viz. crystalline tazobactam sodium monohydrate, can be used in accordance with the invention in the control or prevention of illnesses, especially in the control of β-lactamase-forming pathogens in combination with β-lactam antibiotics, i.e. antibiotics which contain a β-lactam ring, for example penicillins such as ampicillin, amoxicillin, hetacillin, ciclacillin, mecillinam, carbenicillin, sulbenicillin, ticarcillin, piperacillin, apalcillin, mezlocillin, aspoxicillin, talampicillin, bacampicillin, lenampicillin, pivmecillinam, bacmecillinam, carindacillin or carfecillin, preferably ampicillin, amoxicillin, carbenicillin, sulbenicillin, ticarcillin, piperacillin, apalcillin, mezlocillin, aspexicillin or becampicillin, and cephalosporins such as cephalotin, cephaloridine, cefazolin, cefapirin, cephacetrile, ceftezole, cefamandole, cefotiam, cefuroxime, cefotaxime, ceftizoxime, cefmenoxime, ceftriaxone, cefuzoname, ceftazidime, cefoperazone, cefpimizole, cefpira,ide, cefsulodin, cefoxitin, cefmetazole, latamoxef, cefotetan, cefbuperazone, cefminox, flomoxef, cephaloglycin, cephalexin, cefradine, cefatrizine, cefaclor, cefroxadine, cefadroxil, cefprozil, cefuroxime axetil, cefotiam hexetil, cefixime, cefteram pivoxil, cefpodoxime proxetil, ceftibuten, cefetamet pivoxil, cerdinir, cefcamate pivoxll, (6R,7R)-7-[(Z)-2-(2-amino-4-thiazolyl)-2-(methoxyimino) acetamido]-3-(azidomethyl)-8-oxo-5-thia-1-azabicyclo [4.2.0]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-(azidomethyl) -8-oxo-5-thia-1-azabicylo[4.2.0]oct-2-ene-2-carboxylate,

|  | Start | 5° C. | 30° C. | 40° C. | 50° C. | 55° C. | 60° C. | 65° C. |
|---|---|---|---|---|---|---|---|---|
| Lyophilisate | 0.1 | 0.3 | 0.3 | ca. 0.4 |  | ca 0.5 |  | ca. 1.5 |
| Crystalline salt | 0.2 | 0.2 | 0.2 | 0.2 | 0.2 |  | 0.3 |  |

The β-lactamase inhibitory action of crystalline tazobactam sodium coincides with that of the lyophilisate according to EPOS 97 446; through the higher stability of the crystalline salt the pharmacological activity is therefore preserved to a greater extent than is the case with the lyophilisate.

The crystalline tazobactam sodium monohydrate is preferably used in association with a β-lactam antibiotic as medicament for oral or parenteral, preferably parenteral.

The composition of the present invention may be made into tablets, pills, capsules, granules, powders, syrups, lozenges, solutions, suspensions, etc. for oral administration and aqueous, suspending or water-soluble preparations for intravenous, subcutaneous or intramuscular injections.

Carriers useful in formulating the preparations are commonly used pharmaceutically acceptable non-toxic carriers such as gelatin, lactose, starch, magnesium stearate, talc, vegetable oil, animal oil, polyalkylene glycol, etc. The carrier may be used with other additives such as diluents, binders, buffer agents, preservatives, glazes, disintegrators, coating agents, etc.

The preparations can also be presented with the crystalline tazobactam sodium monohydrate in a separate ampoule for dissolution in the aqueous medium presented in a separate ampoule. The crystalline tazobactam sodium monohydrate can be admixed with a β-lactam antibiotic as defined hereinbelow. Thus the crystalline tazobactam sodium monopreferably cephalotin, cephaloridine, cefazolin, cefamandole, cefotiam, cefurexime, cefotaxime, ceftizoxime, cefmenoxime, ceftriaxone, cefuzoname, ceftazidime, cefoperazone, cephalexin, cefaclor, cefuroxime, cefotiam hexetil, cefixime or cefteram pivoxil. Thereby, the crystalline tazobactam sodium monohydrate can be administered before, simultaneously with or after the administration or intake of β-lactam antibiotics. Where the crystalline tazobactam sodium monohydrate is administered simultaneously with a β-lactam antibiotic, then this can be effected by administration as an ad-hoc combination or in the form of a pharmaceutical combination which contain the crystalline tazobactam sodium monohydrate and a β-lactam antibiotic; such pharmaceutical combinations are also an object of the present invention.

The dosage of crystalline tazobactam sodium monohydrate can vary within wide limits and will, of course, be fitted in each particular case to the individual requirements and to the β-lactamase-producing pathogen to be controlled. An approximate range from about 0.25 to 3 g of β-lactam antibiotic per adult per day, and about 0.125 to 2 g per day of crystalline tazobactam sodium monohydrate per adult is exemplary. Weight ratios of crystalline tazobactam sodium monohydrate to β-lactam antibiotic generally range from about 1:10 to about 10:1, preferably about 1:9 to about 3:4. Also more preferred is the ratio of 1:8 to 1:1 of crystalline tazobactam sodium monohydrate to β-lactam antibiotic.

Medicaments containing crystalline tazobactam sodium monohydrate are also an object of the present invention, furthermore also a process for the manufacture of such medicaments which is characterized by bringing crystalline tazobactam sodium monohydrate and, if desired, one or more other therapeutically valuable substances into a galenical administration form; in this connection reference is again made to the pharmaceutical combinations referred to above, which are also an object of the present invention. In particular, pharmaceutical combinations containing crystalline tazobactam sodium monohydrate and the above mentioned β-lactam antibiotics are an object of the present invention. Such combinations are suitable for the control of β-lactamase-forming pathogens.

BRIEF DESCRIPTION OF THE DRAWING

FIG. 1 shows adsorption isotherms of a tazobactam Na-salt lyophilisate.

FIGS. 3-1 and 3-2 show X-ray diffraction diagramme of a crystalline tazobactam Na-salt-monohydrate and its scanning data.

BEST MODE FOR CARRYING OUT THE INVENTION

The present invention will now be illustrated in greater detail with reference to Examples, but the present invention should not be construed as being limited thereto.

EXAMPLE 1

In a 4500 ml 4-neck vessel equipped with mechanical stirrer, thermometer, device for pH-measurement, 500 ml dropping funnel and cooling bath 360.3 g of tazobactam (1.2 moles) obtained according to the method described in EPOS 97 446 were suspended in 720 ml of water. The suspension was cooled with an ice bath to 5° C. and treated with 1200 ml of a 1N aqueous sodium bicarbonate solution added over 2 hours. The pH was adjusted to 4.5. A clear, colorless solution was formed. Stirring was continued for 30 minutes and the pH checked and adjusted to 4.5. Concentration with a rotary evaporator under reduced pressure (bath temperature 35° C. maximum) afforded a viscous oil which contained about 123 g of water. The amount of water was determined by weight difference.

The viscous solution was diluted sequentially with 72 ml of methanol and 1000 ml of acetone at room temperature. The clear solution was transferred into a 6000 ml 4-neck vessel with mechanical stirrer and thermometer and diluted with 1080 ml of acetone. The solution became turbid, and a small amount of seed crystals was added. The mixture was stirred at room temperature overnight during which a white suspension was formed. This suspension was diluted over 3 hours with 2000 ml of acetone, gradually cooled to 5° C. and stirred for A hours at this temperature. The crystals were collected by vacuum filtration on a glass funnel, washed in portions with 400 ml of acetone, dried in an oven under water jet vacuum at 30° C. to constant weight. Yield: 361.4 g of sodium 2α-methyl-2β-(1,2,3-triazol-1-yl)-methylpenam-3α-carboxylate-1,1-dioxide monohydrate as white crystals (88.5%)

Figure 2:
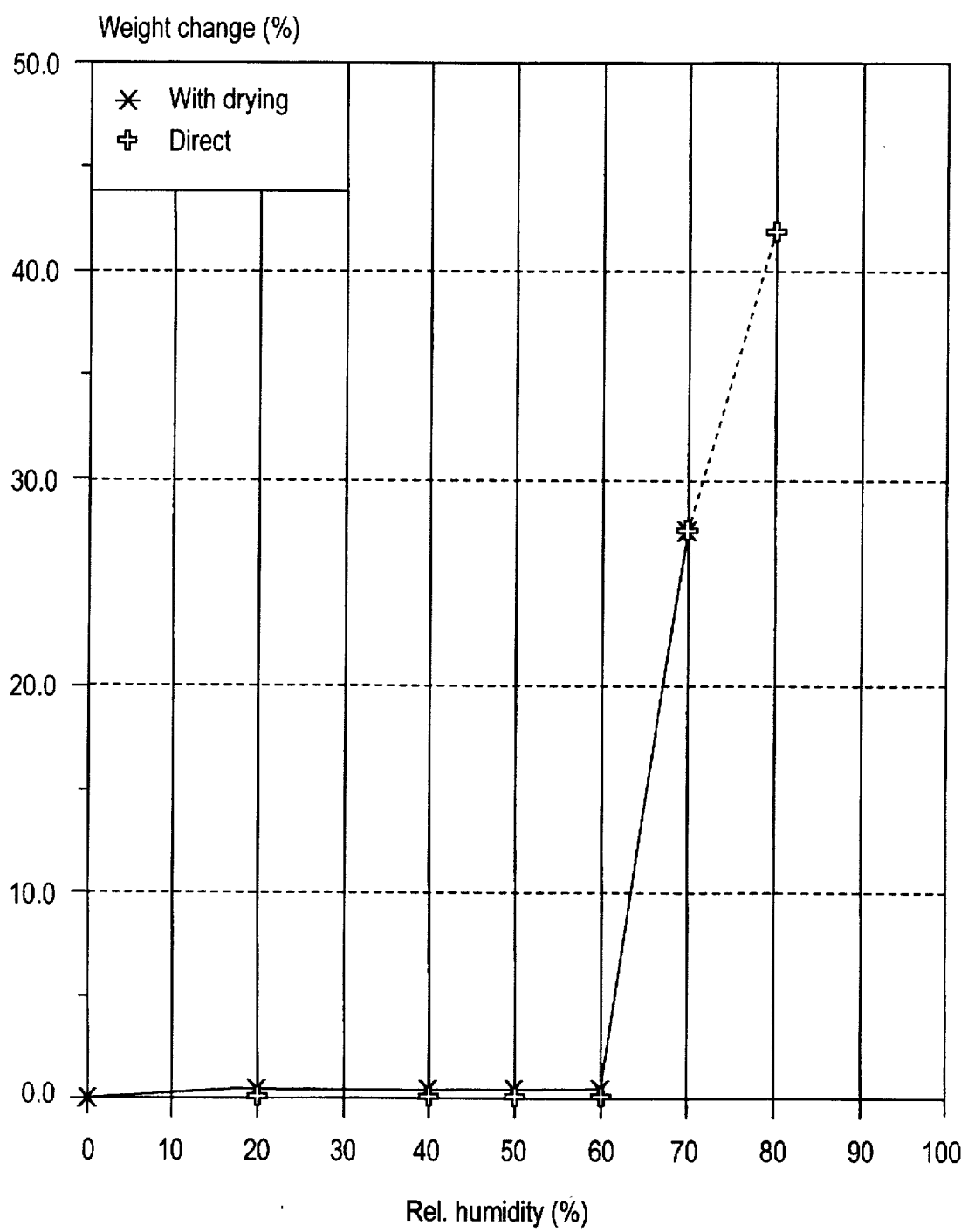
FIG. 2 shows adsorption isotherms of a crystalline tazobactam Na-salt-monohydrate.
Figures 1, 3:
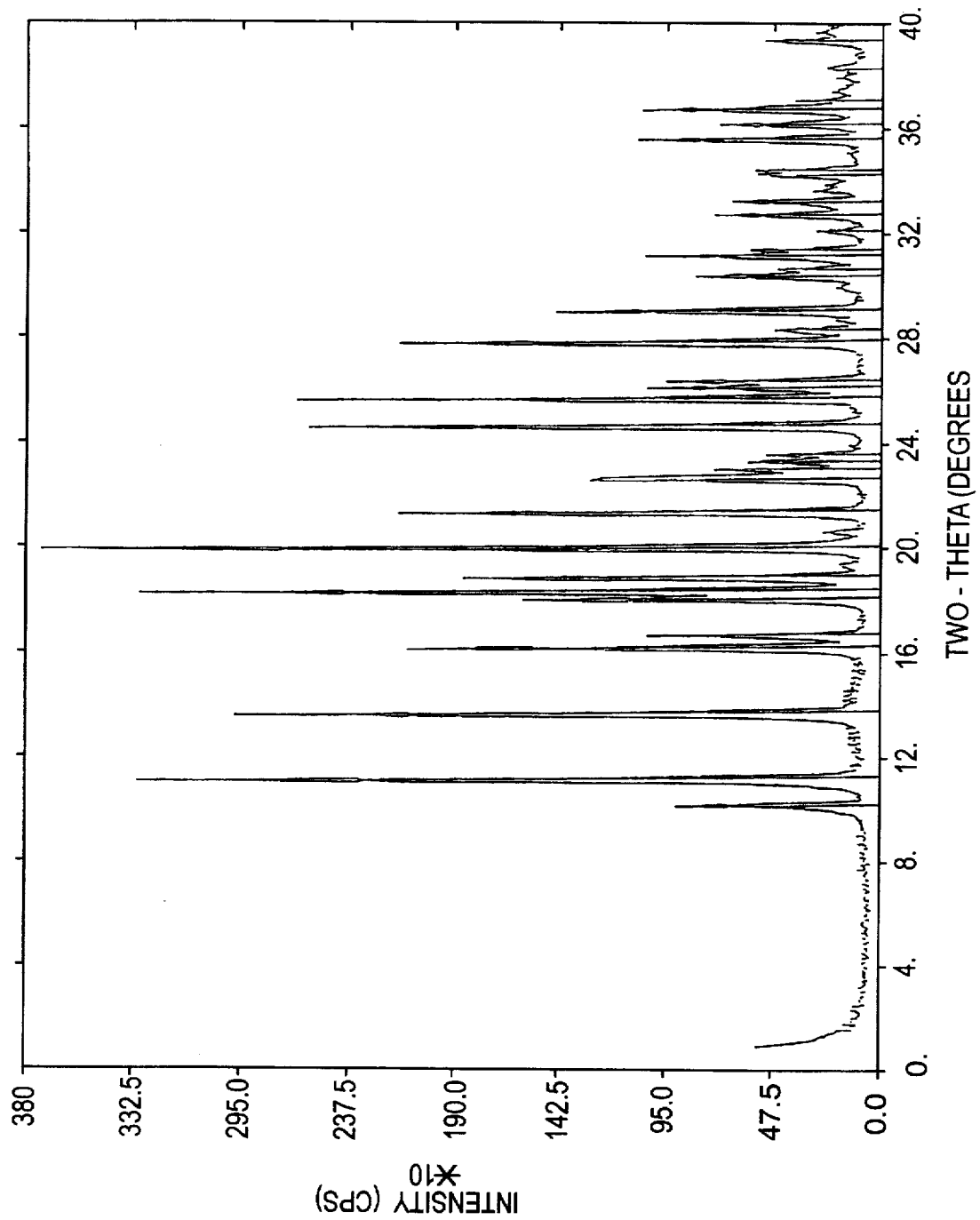

X-Ray diffraction diagramme, see FIGS. 3-1 and 3-2.

| Microanalysis: | calcd % | found % |
| --- | --- | --- |
| C | 35.30 | 35.35 |
| H | 3.85 | 4.17 |
| N | 16.46 | 16.27 |
| S | 9.42 | 9.42 |
| Na | 6.76 | 6.83 |
| water | 5.29 | 5.47 |

EXAMPLE 2

In a 500 ml flask equipped with mechanical stirrer, thermometer, device For pH-measurement, 50 ml burette and cooling bath, 30.0 g of tazobactam (100 mmol) obtained according to the method described in EPOS 97 446 were suspended in 43.0 ml of water. The suspension was treated within 10 minutes with 96.9 ml of a 1N aqueous sodium bicarbonate solution. The pH was adjusted to 4.5. A clear colorless solution was formed. Stirring was continued for 30 minutes and the pH checked and adjusted to 4.5. Concentration with a rotary evaporator under reduced pressure (bath temperature 30°C.) afforded a viscous oil which contained 9.1 g of water. The amount of water was determined by weight difference.

The concentrated solution was diluted with 340 ml of acetone at room temperature. Initially, two phases were formed; by stirring a white suspension was gradually formed. This was stirred for 21 hours at room temperature and filtered over a glass filter. The crystals were washed with 50 ml of acetone and dried in an oven under water jet vacuum at 30° C. to constant weight. Yield 27.9 g of sodium 2α-methyl-2β-(1,2,3-triazol-1-yl)-methylpenam-3α-carboxylate-1,1-dioxide monohydrate as white crystals (82%).

X-Ray diffraction diagramme: identical to Example 1 (FIGS. 3-1 and 3-2)

| Microanalysis: | calcd % | found % |
| --- | --- | --- |
| C | 35.30 | 35.09 |
| H | 3.85 | 3.86 |
| N | 16.46 | 16.59 |
| S | 9.42 | 9.37 |
| Na | 6.76 | 6.85 |
| water | 5.29 | 5.03 |

H-NMR-spectrum δ: 1.23 (s, 3H), 3.10–3.49 (dd, 2H), 3.34 (H$_2$O), 3.89 (s, H), 4.92 (d, 1H), 5.00–5.30 (q, 2H), 7.76 (d, 1H), 7.99 (d, 1H)

Hygroscopicity up to a relative humidity of 60% not hygroscopic (see FIG. 2)

EXAMPLE 3

In a 200 ml 4-neck vessel equipped with mechanical stirrer, thermometer, device for pH-measurement, dropping funnel and cooling bath 10.0 g of tazobactam (33.3 mmoles) obtained according to the method described in EPOS 97 446 were suspended in 43 ml of water. The suspension was cooled with an ice bath to 5° C. and treated with 32 ml of a 1N aqueous sodium bicarbonate solution added over 2 hours. The pH was adjusted to 4.4. A clear, colorless solution was formed. Stirring was continued for 30 minutes and the pH was checked and adjusted to 4.5. Concentration with a rotary evaporator under reduced pressure (bath temperature 35° C. maximum) afforded a viscous oil (13.5 g) which contained 2.8 g of water. The amount of water was determined by weight difference.

This viscous oil was diluted with 2.2 ml water and 120 ml ethanol at room temperature within 3 hours. The product crystallized slowly. The suspension was stirred overnight. The crystals were collected by vacuum filtration on a glass funnel, washed with 10 ml ethanol and dried in an oven under water jet vacuum at 40° C. to constant weight. Yield: 7.0 g of sodium 2α-methyl-2β-(1,2,3-triazol-1-yl)-methylpenam-3α-carboxylate-1,1-dioxide monohydrate as white crystals (61.7%)

X-Ray diffraction diagramme: identical to Example 1 (FIGS. 3-1 and 3-2)

| Microanalysis: | calcd % | found % |
| --- | --- | --- |
| C | 35.30 | 35.03 |
| H | 3.85 | 3.64 |
| N | 16.46 | 16.44 |
| S | 9.42 | 9.38 |
| Na | 6.76 | 6.85 |
| water | 5.29 | 5.54 |

Given below are examples of preparation of the present antibacterial compositions.

| Ampicillin | 200 mg |
| --- | --- |
| Crystalline tazobactam sodium monohydride | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into a capsule.

Preparation Example 2

| Amoxicillin | 100 mg |
| --- | --- |
| Crystalline tazobactam sodium monohydride | 70 mg |
| Lactose | 330 mg |
| Corn starch | 490 mg |
| Hydroxypropyl methyl cellulose | 10 mg |
| Total | 1000 mg |
| | (amount per dose) |

The above ingredients are formulated in the proportions listed above into granules.

Preparation Example 3

| Bacampicillin | 70 mg |
| --- | --- |
| Crystalline tazobactam sodium monohydride | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropyl methyl cellulose | 10 mg |
| Total | 220 mg |
| | (amount per tablet) |

The above ingredients are formulated in the proportions listed above into a tablet.

Preparation Example 4

| Crystalline tazobactam sodium monohydride | 120 mg |
| --- | --- |
| Hydroxypropyl cellulose | 3 mg |
| Corn starch | 25 mg |
| Magnesium stearate | 2 mg |
| Total | 150 mg |
| | (amount per tablet) |

The above ingredients are formulated in the proportions listed above into a tablet.

Preparation Example 5

Manufacture of dry ampoules for intravenous administration:

0.5 g of crystalline sodium 2α-methyl-2β-(1,2,3-triazol-1-yl)-methylpenam-3α-carboxylate-1,1-dioxide monohydrate and 1 g of crystalline ceftriaxone is prepared in the usual manner and filled into an ampoule. Prior to administration the substance mixture is dissolved in 4 ml of physiological saline solution.

If desired, the two active ingredients can be filled separately into two different ampoules.

Preparation Example 6

Manufacture of dry ampoules for intravenous administration:

0.5 g of crystalline sodium 2α-methyl-2β-(1,2,3-triazol-1-yl)-methylpenam-3α-carboxylate-1,1-dioxide monohydrate and 2 g of crystalline piperacillin is prepared in the usual manner and filled into an ampoule. Prior to administration the substance mixture is dissolved in 4 ml of physiological saline solution.

If desired, the two active ingredients can be filled separately into two different ampoules.

INDUSTRIAL APPLICABILITY

As mentioned above, the crystalline tazobactam sodium monohydrate according to the present invention is not hygroscopic and considerably more stable upon storage as compared with the known lyophilisate mentioned above. Thus, the crystalline tazobactam sodium monohydrate is useful as a β-lactamase inhibitory agent in combination with β-lactam antibiotics.

I claim:

1. Crystalline sodium 2α-methyl-2β-(1,2,3-triazol-1-yl)-methylpenam-3α-carboxylate-1,1-dioxide monohydrate (crystalline tazobactam sodium monohydrate).

2. Crystalline sodium 2α-methyl-2β-(1,2,3-triazol-1-yl)--methylpenam-3α-carboxylate-,1,1-dioxide monohydrate (crystalline tazobactam sodium monohydrate) characterized by an X-ray diffraction pattern with peaks at: 10.201, 11.300, 13.820, 16.300, 16.759, 18.141, 18.459, 18.979, 20.061, 21.439, 22.679, 23.060, 23.341, 23.600, 24.739, 25.779, 26.180, 26.421, 27.919, 28.340, 29.079, 30.380, 30.640, 31.178, 31.399, 32.137, 32.779, 33.261, 34.299, 34.480, 35.680, 36.240.

3. Crystalline sodium 2α-methyl-2β-(1,2,3-triazol-1-yl-)-methylpenam-3α-carboxylate-1,1-dioxide monohydrate (crystalline tazobactam sodium monohydrate) according to claim 1 or 2, which is obtainable by adding to a concentrated aqueous solution of sodium 2α-methyl-2β-(1,2,3-triazol-1-yl)--methylpenam-3α-carboxylate-1,1-dioxide (tazobactam sodium) a solvent selected from acetone and ethanol in an amount corresponding to a solvent to water ratio of between about 95:5 v/v and about 90:1 v/v and crystallizing the desired product from the solvent mixture.

4. A process for producing crystalline sodium 2α-methyl-2β-(1,2,3-triazol-1-yl) -methylpenam-3α-carboxylate-1,1-dioxide monohydrate (crystalline tazobactam sodium monohydrate) which is characterized by adding to a concentrated aqueous solution or sodium 2α-methyl-2β-(1,2,3-triazol-1-yl)--methylpenam-3α-carboxylate-1,1-dioxide (tazobactam sodium) a solvent selected from acetone and ethanol in an amount corresponding to a solvent to water ratio of between about 95:5 v/v and about 99:1 v/v and crystallizing the desired product from the solvent mixture.

5. A process according to claim 4, wherein the concentrated aqueous solution contains less than about 0.1 to 0.4 g of water per g of the tazobactam equivalent present.

6. A process according to claim 5, wherein the concentrated aqueous solution contains about 0.25 to 0 35 g of water per g of the tazobactam equivalent present.

7. A process according to any one of claims 4 to 6, wherein the ratio of acetone or ethanol to water is in the range of about 96:4 to 98:2 v/v.

8. A process according to claim 7, wherein the ratio is about 97:3 v/v.

9. A process according to claim 4, wherein the solvent is acetone.

10. A process according to claim 9, wherein the acetone is added in 3 successive volumes at about room temperature, the first volume being about 23 to 27% of the total acetone volume, the second volume being about 24 to 28% of the total acetone volume and the third volume being about 46 to 52% of the total acetone volume.

11. A process according to claim 10, wherein the first volume is about 24 to 25% of the total acetone volume, the second volume is about 26 to 27% of the total acetone volume and the third volume is about 48 to 50% of the total acetone volume.

12. A process according to claim 10 or 11, wherein methanol amounting to about 1 to 4% v/v of the acetone totally added is added together with the first volume of acetone.

13. A composition according to claim 1 further comprising a β-lactam antibiotic.

14. A composition according to claim 1 comprising cephalosporin as the β-lactam antibiotic.

15. A composition according to claim 14 comprising cephalotin, cephaloridine, cefazolin, cefapirin, cephacetrile, ceftezole, cefamandole, cefotian, cefuroxime, cefotaxime, ceftizoxime, cefmenoxime, ceftriaxone, cefuzoname, ceftazidime, cefoperazone, cefpimizole, cefpiramide, cefsulodin, cefoxtin, cefmetazole, latamoxef, cefotetan, ceibuperazone, cefminox, flomoxef, cephaloglycin, cephalexin, cefradine, cefatizine, cefaclor, cefroxadine, cefadroxil, cefprozil, cefuroxime axetil, cefotiam hexetil, cefixime, cefteram pivoxil, cefpodoxime proxetil, ceftibuten, cefetamet pivoxil, cefdinir, cefcamate pivoxil, (6R,7R)-7-[(Z)-2-(2-amino-4-thiazolyl)-2-(methoxyimino)-acetamido]3-(azidomethyl)8-oxo-5-thia-1-azabicyclo-[4.2.0]oct-2-ene-2-carboxylic acid or (E)2-(isobutoxycarbonyl)-2-pentenyl (6R,7R)-7-[(Z)-2-(2-amino-4-thiazolyl)- 2-(methoxyimino)acetamido]-3(azidomethyl)-8oxo-5-thia-1-azabicyelo[4.2.0]oct-2-ene-2-carboxylate.

16. A composition according to claim 15 comprising cephalotin, cephaloridine, cefazolin, cefamandole, cefotiam, cefurexime, cefotaxime, ceftizoxime, cefmenoxime, ceftriaxone, cefuzoname, ceftazidime, cefoperazone, cephalexin, cefaclor, cefuroxime, cefotiam hexetil, cefixime or cefteram pivoxil.

17. A composition according to claim 13, wherein the weight ratio of the crystalline tazobactam sodium monohydrate to the β-lactam antibiotic is from about 1:10 to 10:1.

18. A composition of claim 17, wherein the weight ratio of the crystalline tazobactam sodium monohydrate to the β-lactam antibiotic is from about 1:9to 3:4.

19. A composition of claim 17, wherein the weight ratio of the crystalline tazobactam sodium monohydrate to the β-lactam antibiotic is from about 1:8 to 1:1.

20. A composition according to claim 13 as a combination preparation for the simultaneous, separate or successive administration in antibacterial therapy.

21. A method for controlling or preventing bacterial infections which comprises administering to human or mammals in need of such control or prevention an effective amount of a compound according to claim 1 or 2, together with a β-lactam antibiotic and pharmaceutical acceptable carrier.

22. A composition for controlling bacterial infections comprising an effective amount of crystalline sodium 2α-methyl-2β-(1,2,3,-triazol-1-yl)-methylpenam-3α-carboxylate-1,1-dioxide monohydrate (crystalline tazobactam sodium monohydrate) and a pharmaceutically acceptable carrier.

23. The composition of claim 22 wherein the crystalline tazobactam sodium monohydrate is characterized by an X-ray diffraction pattern with peaks at: 10.201, 11.300, 13.820, 16.300, 16.759, 18.141, 18.459, 18.979, 20.061, 21.439, 22.679, 23.060, 23.341, 23.600, 24.739, 25.779, 26.180, 26.421, 27.919, 28.340, 29.079, 30.380, 30.640, 31.178, 31.399, 32.137, 32.779, 33.261, 34.299, 34.480, 35.680, 36.240, 36.819, 37.140, 38.320, and 39.400.

24. A composition according to claim 13, wherein the β-lactam antibiotic is penicillin.

25. A composition according to claim 24, wherein said penicillin is ampicillin, amoxicillin, hetacillin, ciclacillin, mecillinam, carbenicillin, sulbenicillin, aspoxicillin, talampicillin, bacampicillin, lenampicillin, pivmecillinam, bacmecillinam, carindacillin, carfecillin.

26. A composition according to claim 24, wherein said penicillin is ampicillin, amoxicillin, carbenicillin, sulbenicillin, ticarcillin, piperacillin, apalcillin, mezlocillin, aspexicillin, becampicillin.

27. A composition according to claim 24, wherein the weight ratio of the crystalline tazobactam sodium monohydrate to the β-lactam antibiotic is from about 1:10 to 10:1.

28. A composition according to claim 24, wherein the weight ratio of the crystalline tazobactam sodium monohydrate to the β-lactam antibiotic is from about 1:9 to 3:4.

29. A composition according to claim 24, wherein the weight ratio of the crystalline tazobactam sodium monohydrate to the β-lactam antibiotic is from about 1:8 to 1:1.

30. A composition according to claim 24, as a combination preparation for the simultaneous, separate or successive administration in antibacterial therapy.

* * * * *

UNITED STATES PATENT AND TRADEMARK OFFICE
CERTIFICATE OF CORRECTION

PATENT NO. : 5,763,603
DATED : June 9, 1998
INVENTOR(S) : G. Trickes

It is certified that error appears in the above-identified patent and that said Letters Patent is hereby corrected as shown below:

Column 5, line 18, after "shows" insert --22°C--.

Column 5, line 20, after "shows" insert --22°C--.

Column 10, line 48, change "aspexicillin" to --aspoxicillin--.

Column 10, line 48, change "becampicillin" to --bacampicillin--.

Signed and Sealed this

Twenty-third Day of February, 1999

Attest:

Q. TODD DICKINSON

*Attesting Officer*    *Acting Commissioner of Patents and Trademarks*